(12) United States Patent
Zeinfeld

(10) Patent No.: US 8,341,179 B2
(45) Date of Patent: Dec. 25, 2012

(54) SYSTEM AND METHOD FOR CONTENT COLLECTION AND DISTRIBUTION

(76) Inventor: Michael Zeinfeld, Chicago, IL (US)

( * ) Notice: Subject to any disclaimer, the term of this patent is extended or adjusted under 35 U.S.C. 154(b) by 124 days.

(21) Appl. No.: 12/831,143

(22) Filed: Jul. 6, 2010

(65) Prior Publication Data

US 2011/0010386 A1     Jan. 13, 2011

Related U.S. Application Data

(60) Provisional application No. 61/270,547, filed on Jul. 9, 2009.

(51) Int. Cl.
*G06F 7/00*     (2006.01)

(52) U.S. Cl. ...................................................... 707/769

(58) Field of Classification Search ................ 707/705, 707/706, 722, 736, 758, 769, 759, 770, 999.104; 705/1–2, 26; 455/414.1

See application file for complete search history.

(56) References Cited

U.S. PATENT DOCUMENTS

| | | | |
|---|---|---|---|
| 2007/0208583 A1* | 9/2007 | Ward | 705/1 |
| 2008/0214157 A1* | 9/2008 | Ramer et al. | 455/414.1 |
| 2008/0306768 A1* | 12/2008 | Fotsch et al. | 705/2 |
| 2009/0106117 A1* | 4/2009 | Porter et al. | 705/26 |

* cited by examiner

*Primary Examiner* — Hung T Vy

(74) *Attorney, Agent, or Firm* — White-Welker & Welker, LLC; Matthew T. Welker, Esq.

(57) ABSTRACT

Content delivery system that aggregates and delivers text, audio and video and other content to an end-user from a library of past and current content. A user can actively provide information to the system without utilizing multiple steps or the system can guide content creation from a content originator. A single or limited action content request from a user to the content originator simultaneously collects various information from the user without additional user action. The system collects implicit and explicit content from the source where a content originator can indicate content that should appear a delivery system which originates on other delivery systems. The system automatically reads content and assigns it to a specific category and allows the content originator to further edit said content. Content is delivered to a user through implicit and explicit triggers and excludes content or makes available content depending on user history and other variables.

27 Claims, 7 Drawing Sheets

SYSTEM AND METHOD FOR CONTENT COLLECTION AND DISTRIBUTION

CROSS REFERENCE TO RELATED APPLICATIONS

This application claims priority from U.S. Patent Application Ser. No. 61/270,547, entitled "Content collection and distribution system", filed on 9 Jul. 2009. The benefit under 35 USC §119(e) of the United States provisional application is hereby claimed, and the aforementioned application is hereby incorporated herein by reference.

SEQUENCE LISTING OR PROGRAM

Not Applicable

FEDERALLY SPONSORED RESEARCH

Not Applicable

TECHNICAL FIELD OF THE INVENTION

The present invention relates to search queries over a network and user configuration of feeds and clusters in conjunction with a computing device. More specifically, the present invention relates to a user's personalized content consumption, web browsing and search experience.

BACKGROUND OF THE INVENTION

There are many methods to allow people to stay in touch with people such as friends, family, colleagues celebrities, brands and companies. Such methods include television, the Internet, the radio, and live interactions, for example. Many of these services are subscription based to which people "subscribe".

Broader based methods such as television and radio provide another method to keep informed with others. For example, users may follow a celebrity on a television show or listen to an interview with a celebrity on the radio. It is also common that older forms of communication such as television and radio are supplemented and/or complimented with the use of new communication tools and platforms such as social networks enabled by the Internet.

These broader based methods such as television and radio are less than ideal because it is entirely one way. The user can listen or watch the television, for example, but there is no way to select what sub-set of information they want to receive or provide any feedback to the information source.

Online methods such as social networking systems such as TWITTER, FACEBOOK and others provide a platform for users to distribute personal information to others who choose to receive that information. Users can stay in touch with both people they know as well as celebrities they want to follow through these methods.

Users use social networking to stay in touch with others as well as to use to find information about their lives. However, because these social information systems are usually one way and not dependent on context, information is lost. For example, if a first user is looking for a good restaurant but second user has already sent the network information about a good restaurant previously, there is no way to easily provide access to this information when a user, such as the first user needs it.

Additionally, these social networking systems are dependent on actively participating as opposed to collecting implicit behaviors and thoughts which may be complementary. For example, a first user may be in Chicago, and if the first user wants to know what a given celebrity thinks about Chicago, the first user would have to actively request from the information source, if such a process existed, to find out what a given celebrity thinks about Chicago, for example a given celebrity's favorite restaurant in Chicago.

Another example of a reason to keep informed with others in the medical industry. For example, someone who was just diagnosed with cancer, may want to keep informed with a specific doctor who has an expertise in cancer. Perhaps the doctor has previously given lectures that contain helpful information to assist people who have been diagnosed with cancer. Or, perhaps the doctor has sent out messages on a social networking system that pertain to getting diagnosed with cancer. The patient may start to follow the doctor, but their timelines are out of sync.

Additionally, current content distribution systems usually rely on the user actively seeking the information. For example, they must turn on a television, visit a web-site, turn on the radio. For example, if a first user is in Chicago and wants to find out what a given celebrity's favorite restaurant is in Chicago, they would have to search the a given celebrity's web-site to find out if such information exists. This is not optimal because a given celebrity may not have information related to the user's search, or the user may visit the restaurant in Chicago and—even though the information exists on a given celebrity's web-site, the user may never visit a given celebrity's web-site and discover such helpful information.

DEFINITIONS

The term CONTENT ITEM generally refers to any information, be it text, visual, audio, touch, or any combination thereof, that is created or provided to the system by a Content Provider.

The term CONTENT PROVIDER and CONTENT ORIGINATOR generally refers to an individual person, group of individuals, organization, or other entity (including a computer or computer system), that employs the system and method of content collection and distribution taught by the present invention via a telecommunication system, or by a computerized information processing system, for the creation, submission, sharing, and/or transfer of content information.

The term USER generally refers to an individual person, group of individuals, organization, or other entity (including a computer or computer system), that employs the system and method of content collection and distribution taught by the present invention via a telecommunication system, or by a computerized information processing system, for the transfer of information.

The Content Provider may also be a User of the system and method taught by the present invention. A Content Provider and a User may or may not be located in the same location.

SUMMARY OF THE INVENTION

Techniques are disclosed herein to enrich a user's personalized content consumption, web browsing and search experience by incorporating the user's current activity, social relations and association histories as well as historical search and browsing data to personalize many aspects of the user's mix of mobile content and configuration of information displayed on the user's device or aggregated on a personalized home page. These techniques may be automatically applied, or performed by the user. A content object may be any form or format of content that is consumable by users such as, but not limited to, any one or more of the following: text, numerical data, images, animation, audio, video or any combination thereof including content encountered as search results, through browsing or from communications with others through voice, email, text, image, animation, gesture, audio or video. Content may come from any data processing source or device.

This system of the present invention contains the following features: A content delivery system that aggregates and delivers text, audio and video and other content to an end-user from a library of past and current content.

A method which a user can actively provide information to the system without utilizing multiple steps.

A method with which the end user can provide implicit or explicit feedback to the delivery system so that the content can be more relevant.

A method with which to collect implicit and explicit content from the source. A method with which to guide content creation from a content originator.

A method with which a content originator can indicate content that should appear a delivery system which originates on other delivery systems.

A method which automatically reads content and assigns it to a specific category and may allow the content originator to further edit said content.

A method with which content can be delivered to a user through implicit and explicit triggers.

A method with which to easily duplicate this process to other content sources and users.

A method which excludes content or makes available content depending on user history, user class and other variables. A single or limited action content request from a user to the content originator which would simultaneously collect various information from the user without additional user action.

BRIEF DESCRIPTION OF THE DRAWINGS

The accompanying drawings, which are incorporated herein and form a part of the specification, illustrate the present invention and, together with the description, further serve to explain the principles of the invention and to enable a person skilled in the pertinent art to make and use the invention.

DETAILED DESCRIPTION OF THE INVENTION

The following description is demonstrative in nature and is not intended to limit the scope of the invention or its application of uses. There are a number of significant design features and improvements incorporated within the invention. The current invention is a system and method for content collection and distribution System. This system allows users to subscribe to content providers giving access to past and current content with minimal effort and constructively. In one embodiment, an individual, (also referred to as a "User") initiates a machine running a program, such as a web site or downloads a mobile application. Such application may be on a network or contain a program which is on a local User machine running a program, both powered by the system of the present invention. In this document the program which the machine is running will be referred to as an "Application" 10.

The Application 10 represents a content item 11, which may be a specific individual, such as a celebrity or group of celebrities, or a concept such as a brand, for example, or a company or a group of companies, "Content Originator 12" or collectively "Content Originators 12". The User may customize these Content Originators 12 on the Application 10. For example, if the User chooses a sports team as the Content Originator 12, the User can select a specific player of the sports team. Or, for example, if the User chooses a brand, such as APPLE, they can select specific products of APPLE, such as the IPHONE.

Figure 1:
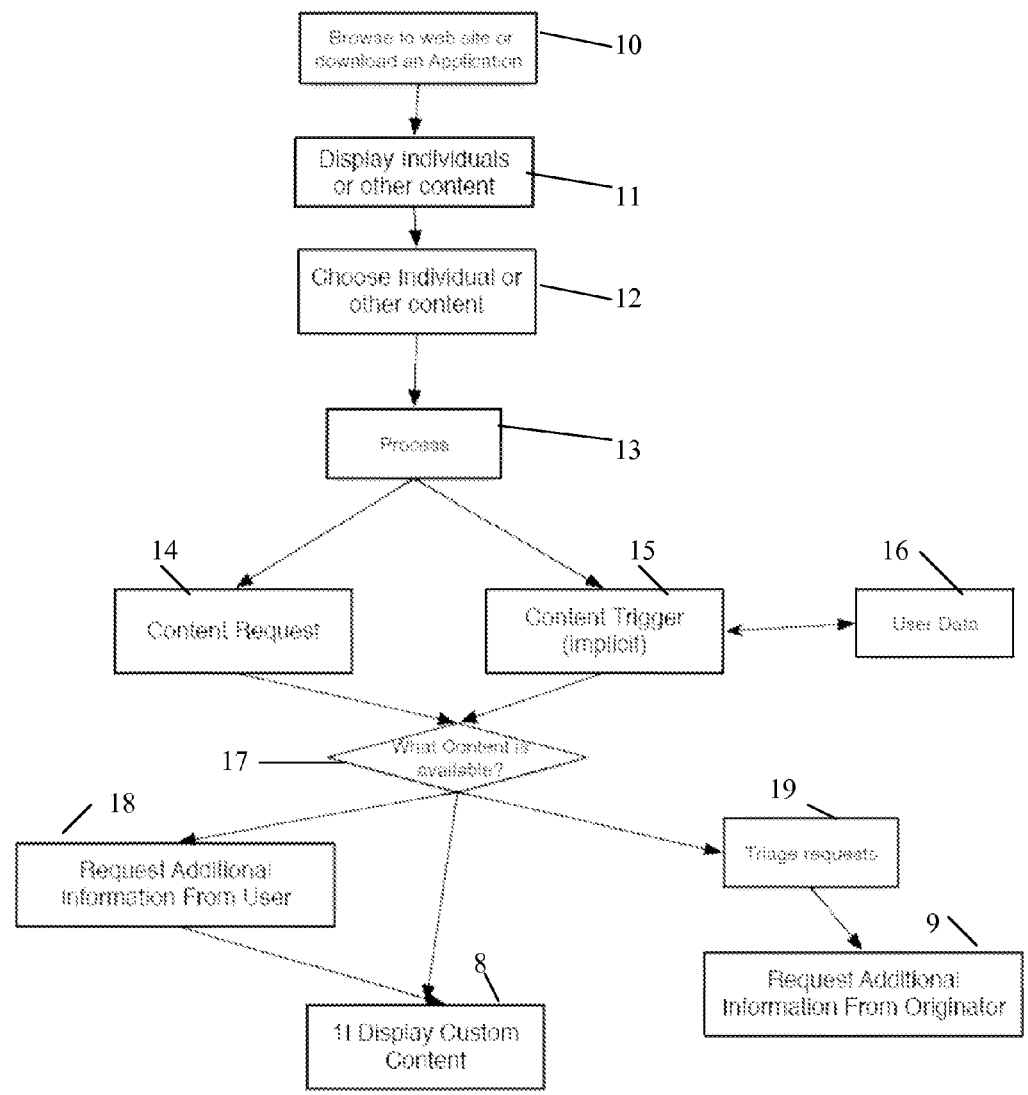
FIG. 1 discloses a flow diagram of dynamic content display.

Now referring to FIG. 1, after the User selects a Content Originator 12, the system of the present invention begins to collect and process information from the User ("User Information"), which may be stored in a database in step 13. This information may be Implicit (Implicit Information 21), in other words the user may not overtly enter information into the system of the present invention. For example but not limited to, this information may be the User's location (latitude and longitude), the date and time of the information request, User facial expressions, User biometric data, and the amount paid for the App, or information retrieved from other sources which may relate to the User. 10. Or, for example, the system of the present invention may even scan the user's fingerprint to determine additional information about the user. The application 10 can obtain medical data from electronic medical records or medical data from devices such as a blood pressure device or other diagnostic device. Additionally, the application 10 can obtain information from any other third party source.

The User may create a content request 14 from the Application 10. This content request may be an explicit query, by touching a button. In other words, a User may download an Application 10 related to a celebrity and make a general content request to the celebrity.

The content request may also be implicit as shown in step 15. In other words, the content request may automatically be pushed out to the User from the system of the present invention based on implicit information such as the User's location.

When a content request occurs, either implicitly as shown in step 15, explicitly as shown in step 14 or otherwise, the system of the present invention will query a database 16 for content which applies to the User. Note that in this case the system of the present invention is beginning the process with content in order to determine what to display to the user. Content may be prioritized in the database, for example by a prioritization field or by some other information such as the amount of content that exists or by past behavior of other users which may or may not be similar to the User.

For example, if a User is using an Application 10 related to a celebrity, and the User is in Chicago, the Application 10 may query the database 16 to determine if there is information in the database 16 about the celebrity and Chicago and what content is available as shown in step 17. The system of the present invention will search past content using a latitude and longitude field, for example, for content that is within a specified distance from the User.

Based on the available content, the system of the present invention will determine if other information is needed from the user to display content. If only one content item, or other small number of content items, for example, exists across the entire database 16 for the Content Originator 12, the system of the present invention may display that content. If the system of the present invention only knows that the User is in a specific geography, for example, the system of the present invention will query to see if there is content related to the Content Originator 12 related to that geography.

For example, if the Application 10 is related to a celebrity and the user is in Chicago, the system of the present invention may check to see if there is information related to that celebrity in Chicago. If there is only one content item related to that celebrity in Chicago, the Application 10 may display that content. If there are multiple content items available, the Application 10 may request additional information from the user in order to narrow the search. For example, if in the database there is information about the celebrity and what restaurants the celebrity likes in Chicago as well as what bars the celebrity likes in Chicago, the system of the present invention will request more specificity from the User as shown in step 18, for example, if they are interested in bars or restaurants. Note that the system of the present invention will use the content that is available to formulate the request and, subsequently, what content is displayed.

Additionally, the Application 10 may also request additional information in step 18 from the User related to the User's interests. For example, there may be a general question included with the information request such as "what do you want to know about?". The User can answer this question. The answers will be stored in a database 16 for later use to determine additional information from the Content Originator 12. Additionally, the User request may be stored in a database 16 for later use.

This information request 18 can be triaged and sorted by category as show in step 19. For example, if many requests on a specific topic are collected, this information request may be sent to the Content Originator 12. For example, a User may ask the sports celebrity what they think about a competitive team winning a big game, for example. If the information is not in the database, the user Request will be stored in a database 16 with fields such as Topic, User and which content originator 12 to which it applies.

A content request may immediately be sent to the Content Originator 12 for response in step 9. The Content Originator 12 may be running the system of the present invention on a mobile device where the Content Originator 12 may provide the content. Or, all content requests, for example, may be triaged in step 19 so that only requests that match a specific criteria will be sent to the content originator.

The triage criteria in step 19 may be the number of requests based on a specific key word or topic. Or, specific keywords or topics may trigger the request. Or, specific classes of users may trigger the request. For example, if a User has paid more for the Application 10, their requests may take priority. Or, for example, if the Content Originator 12 has placed the User in a specific class of users where they would like to respond. For example, the sports player may choose to receive requests from other celebrities.

Additionally if there are other Content Originators 12 in the system which may be able to answer the questions, the request may be sent to them as well. Content Originators 12 can designate other users to answer requests, for example, even on their behalf.

When content is displayed to the User in step 8, it may be in any form, such as video, audio, text, links to other content, voice, GPS information, for example.

Figure 2:
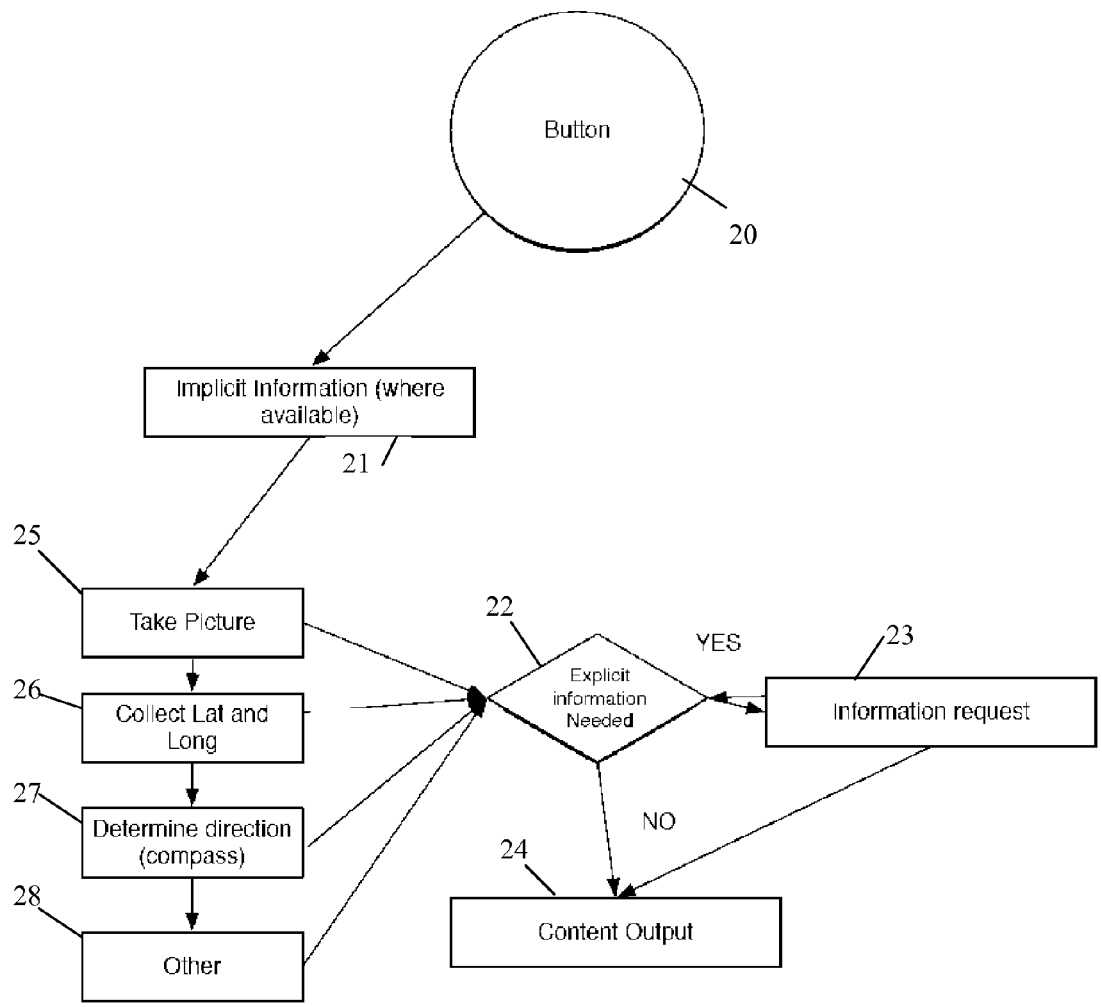
FIG. 2 discloses a diagram of a single action content request.

Now referring to FIG. 2, the User may initiate a request using a single-button system 20. When the User initiates a request, the system of the present invention may simultaneously collect implicit information for later user as shown in step 21, including but not limited to a picture 25, latitude and longitude 26, compass direction 27, or other information 28.

The system of the present invention may use these values to create a sub-set of content 21 that is available to the User. For example, the system of the present invention may use latitude and longitude to search the content database 19 of the content originator 12 for content entries that are within a certain distance of the User. The system of the present invention may use a photograph of the user's surroundings to determine what the User is looking at, which may, in turn, search a database for photographic data which matches (exactly or approximately) photographic data corresponding to content associated with the content originator, for example.

Depending on the results of the query, the system of the present invention may request additional information from the User. For example, if the User is viewing a baseball stadium in Chicago facing east, viewing the scoreboard, the system of the present invention will extract a list of content items related to a Content Originator 12 that match exactly or match approximately the information supplied by the User.

The system of the present invention may then "stack" the relevant content items as a query in the database, and list the sub-set of topics and/or questions that the content relates to. For example, if the Content Originator 12 is a baseball player, the system of the present invention would query the content and may develop a list of content which may include opinions about the stadium, best experiences in that section of the field, knowledge that the content originator has about that section of the field, even pictures or videos of the content originator in that section of the field.

The system of the present invention may then match and/or stack this information to past User history, implicit information, or data to narrow down the list of topics using, for example, previous logs on topics which the User has requested. For example, if there is a database log of the User requesting topics related to architecture, than content related to the history of the stadium will be prioritized to display to the User.

Or, for example, the Content Originator 12 may have previously indicated a content priority (by topic or by individual content). Or, for example, the content topics can display in order of rating from other users.

Additional information may be requested from the User by the system as shown in step 23 of the present invention, for example asking the user to choose a topic.

The system of the present invention may ask for more explicit information as shown in step 22.

In step 24, the system of the present invention determines the optimal content to display, based on number of content items, for example, or even type of content, the system of the present invention may display the content.

Figure 3:
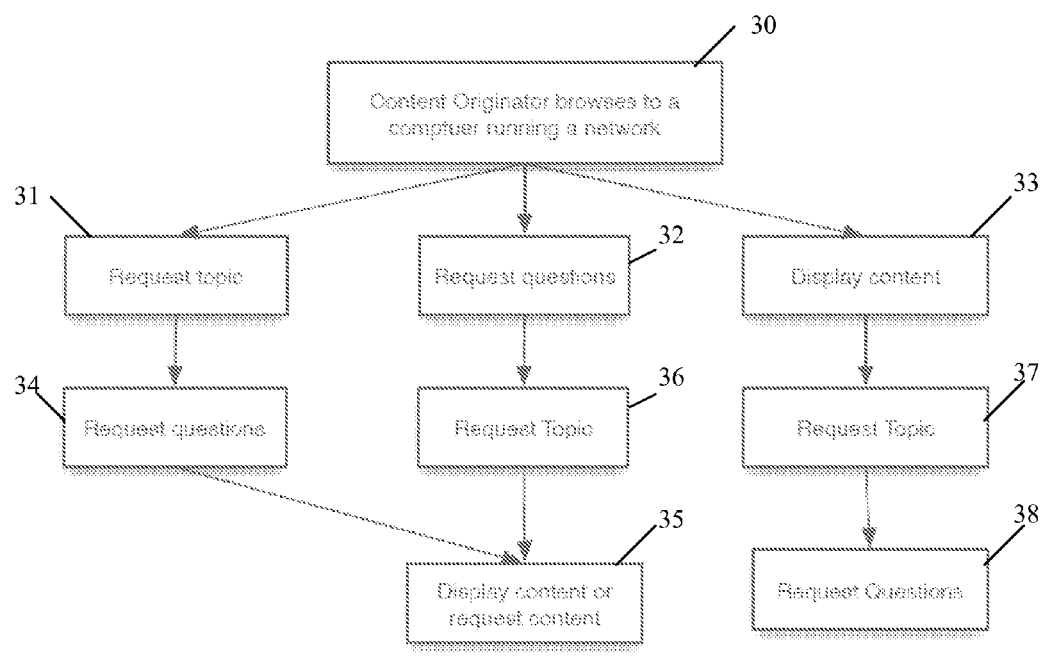
FIG. 3 discloses a flow diagram for content retrieval.

Additionally, there may be a process to explicitly collect information from the Content Originator 12, which can be stored in the database 16 for later display to the User as show in FIG. 3. For example, the Content Originator 12 may be presented with a series of questions, which are aimed to find out more information from the Content Originator 12 for later use after browsing to a computer running the system in step 30.

Upon the Content Originator 12 for later use after browsing to a computer running the system in step 30 the content originator may either request a topic 31, request questions 32, or view displayed content 33.

After listing topics requested in step 31, the system of the present invention may query a database of topics from other content originators and display this list 35 to the Content Originator 12. Additionally, the Content Originator 12 may add his or her own questions in step 34. The Content Originator 12 may answer these questions and topics in step 34, or, for example, or link content that may already be in the system, or, for example, provide new links to new topics.

For example, a famous fitness instructor may log into the system of the present invention in step 30. He may list a series of questions that people usually ask him in step 32, such as "should I work out after eating?" and "what is the best exercise for a hot day?". The system of the present invention may search the database for other similar questions by keyword, for example, and the system of the present invention may automatically connect the questions to other questions in the database using keywords, and their associated data, such as what topic they belong to as shown in step 36. (For example, the question "should I work out after eating" may belong to the topic "Work out processes".)

Also, at this point, the system of the present invention may search the internet for content related to the Content Originator 12, from which the Content Originator 12 may assign display content 33 to request questions 38 and request topics 37. Or, for example, the Content Originator 12 may provide new content or links to content directly in the system of the present invention.

Figure 4:
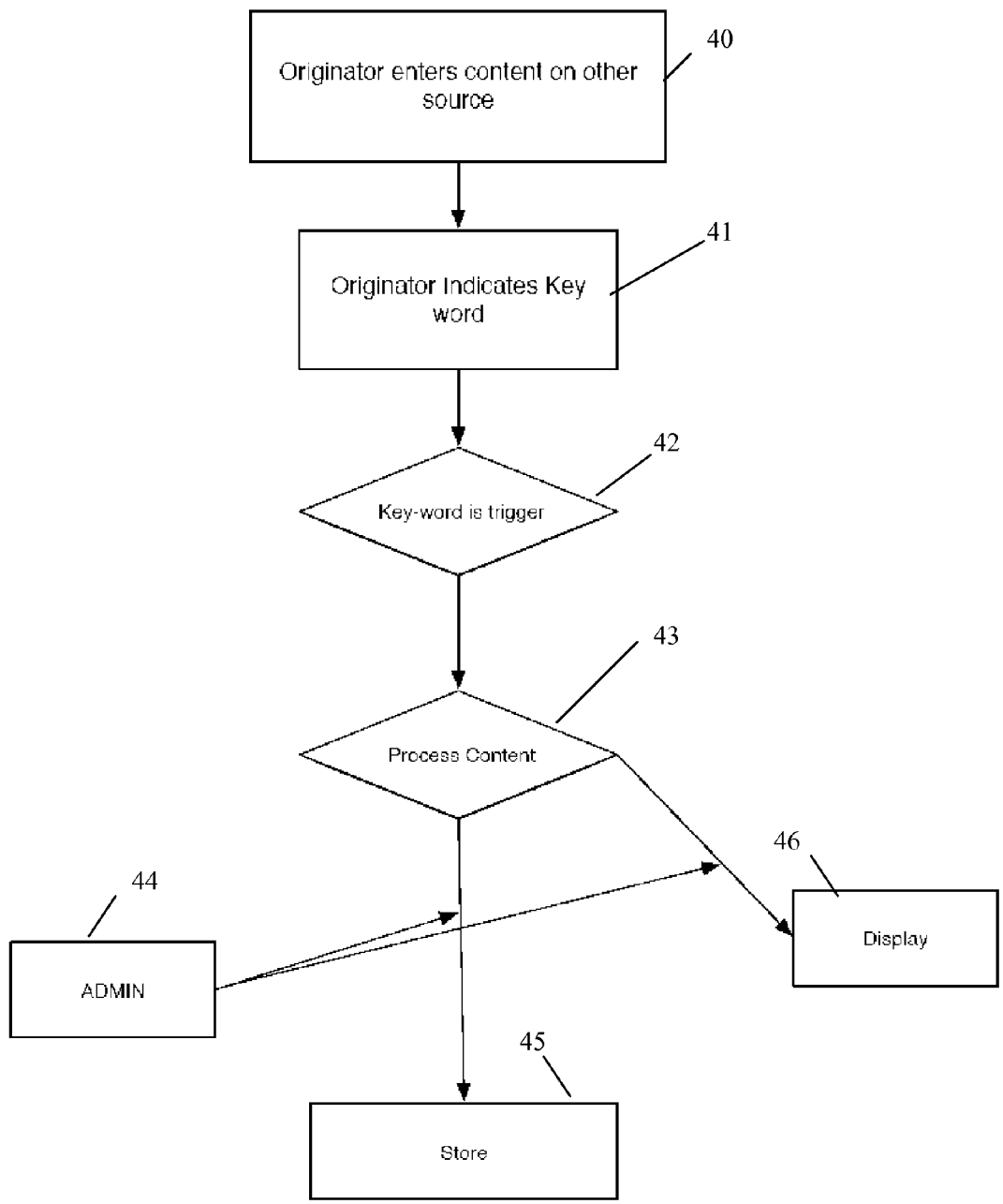
FIG. 4 discloses a flow diagram of continuous content aggregation.

Now referring to FIG. 4, additionally there may be a process so that the Content Originator 12 can tag content on other sources so that the system of the present invention can efficiently pull information from other content sources, which may include other web-sites, personal emails, social networking sites, television appearances, and more.

The content originator 12 may add content on another source 40, such as a social networking website. The system of the present invention will read this content through an automated process for example, such as an XML search or RRS feed. The system of the present invention may know about the feed because it was entered into the system of the present invention by the Content Originator 12, another user or even an administrator, for example. Or, the system of the present invention, for example, may search the Internet for content that may be relevant to the Content Originator 12.

The system of the present invention may add the Content or search the content for keywords or other indicators that may have been pre-defined by the system of the present invention in step 41. If such keywords exist in the content, the system of the present invention may execute pre-defined scripts, such as push notifications, after identifying the keyword trigger 42 to process the content in step 43. For example, a pre-defined keyword may trigger automatically display the content to the user. Or, for example, the keyword may indicate that the content should be stored for later use in a specific category. The Content Originator 12 overtly or non-overtly may include the keyword.

Keywords may also be behavioral, for example, such that any content developed in Chicago, for example, is automatically processed according to pre-defined processes.

An admin or other users, for example, may have the ability to further refine the content as shown in step 44 so that it is more efficiently displayed by the system of the present invention in step 46.

Additionally, the system of the present invention will store the content for later use as shown in step 45 or, perhaps display the content directly to users as shown in step 46.

By way of example of above, a music star may be on a social web site, such as TWITTER, for example. He currently may be twittering about various content subjects, such as his current rock tour as well as about other items in his life. The system of the present invention may search his entries for specific keywords, such as a specific hypertext link, for example, which would indicate to the system of the present invention that the content should be displayed immediately to the user network. The link, may for example, be a link to the Application 10 so that viewers of the social networking site can be directed to the download the Application 10. This would have the added utility of a assisting the system of the present invention in content processing as well as promoting the Application 10 at the same time. If the link does not exist, the system of the present invention will store the data for later display to the user network.

Or, as another example if the user submits "I'm on vacation" and another website or computer running a program. The Application 10, for example, can look for keywords and then respond with content related to the keywords, if it exists. The Application 10 can also scan medical records, for example, and respond with the correct content Inputs into the system of the present invention may be any form, implicit or explicit, for example, audio (speaking), video (taking a picture and matching information using visual data), or otherwise. Similarly, a process exists to efficiently display content to the user.

Figure 5:
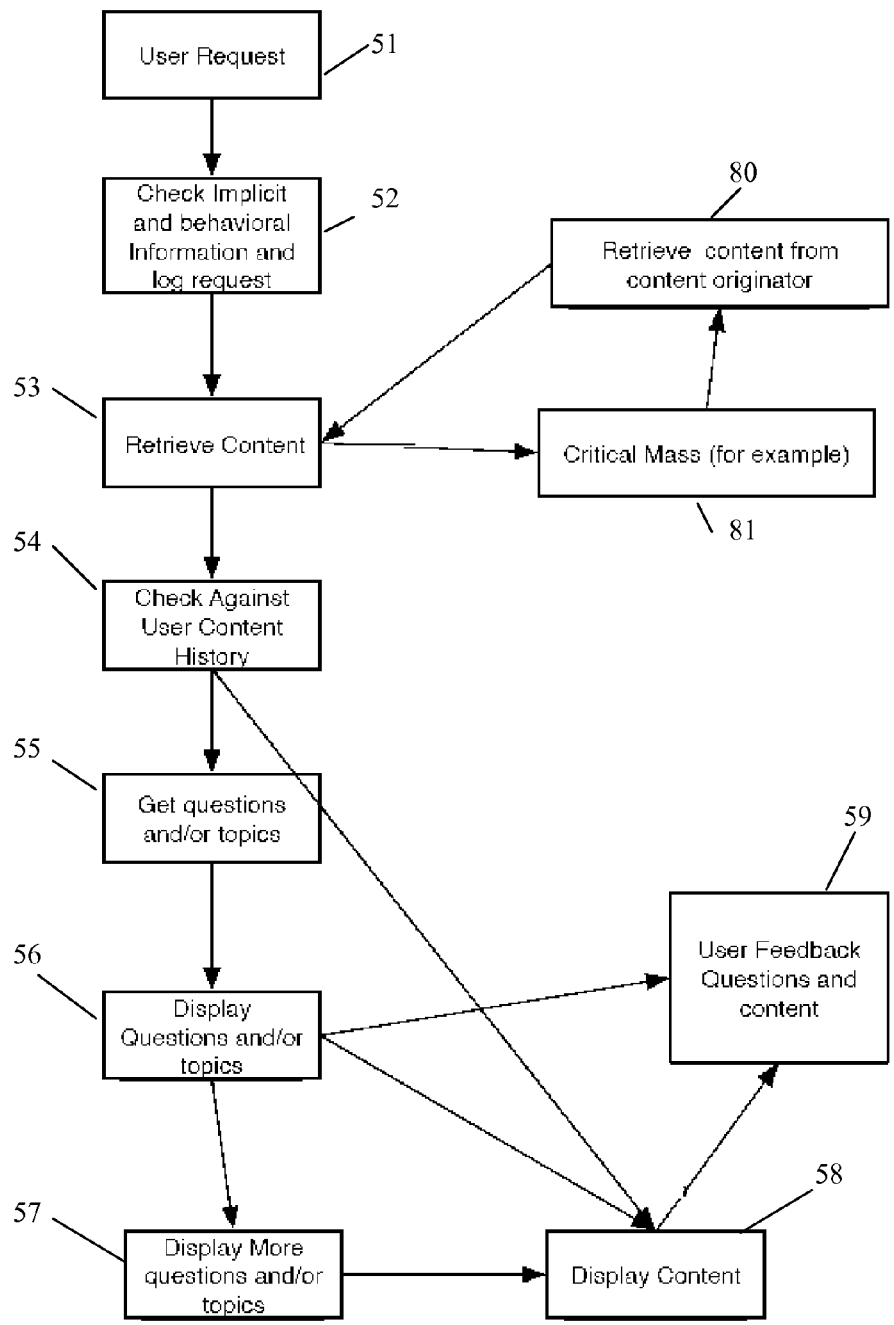
FIG. 5 discloses a flow diagram of process for dynamic question development.

Now referring to FIG. 5, the process for dynamic questions development is illustrated. In step 51a user request occurs for content. This user request may either be explicit or implicit which is checked by the system in step 52. For example, the user may specifically ask the system of the present invention for content, or the user may trigger the request through another means, such as entering a specific geography, for example.

The system of the present invention in step 52 may check the database for other relevant behavioral information, such as but not limited to, when they last checked the system of the present invention for content, past responses to other questions, what content has appealed to them, what content is in the database when they first activated the Application 10, etc.

Appropriate content will be retrieved from the database. If content does not appropriately match the user request in the database, the system of the present invention may log this request. In step 81 the system of the present invention may use a decision criteria such as the amount of related content requests as well as the status of the user (the user may belong to a class that would require an immediate content request to the content originator).

In step 80 the system of the present invention may send an information request to the content originator, where the content originator can respond. When the content originator responds, this content may be stored in the database. Additionally, the user may be alerted that the content now exists.

The system of the present invention may query the database for content that the user has and hasn't seen. The system first checks against a user content history in step 54 what the user has and hasn't seen. The system may display this content in step 58. Next the system will return the query results for questions and topics in step 55 and display the questions and or topics in step 56. The system of the present invention may only display content and content topics and questions that the user has not seen. The user can also choose to see all content, regardless if he or she has seen the content previously, for example.

The system of the present invention may then, for example but not limited to, use a criteria such as the amount of content available, or past user preferences to determine if content should be displayed to the user, or if additional questions or topics should be displayed to the user before content is displayed as shown in step 57. For example, if only one content item exists, there would be no sense in asking additional questions to the user, the system of the present invention may in that case, simply display the content. One key thing is that the system of the present invention is determining what content is available, among other things, and using that content sub-set to determine what to display next to the User as shown in step 56 or what question to ask the User next as shown in step 57

Content is displayed to the User in step 58. Additionally, the User is provided an opportunity to provide feedback to the system of the present invention if content, questions, topics are relevant to the current set of User circumstances as shown in step 59.

Figure 6:
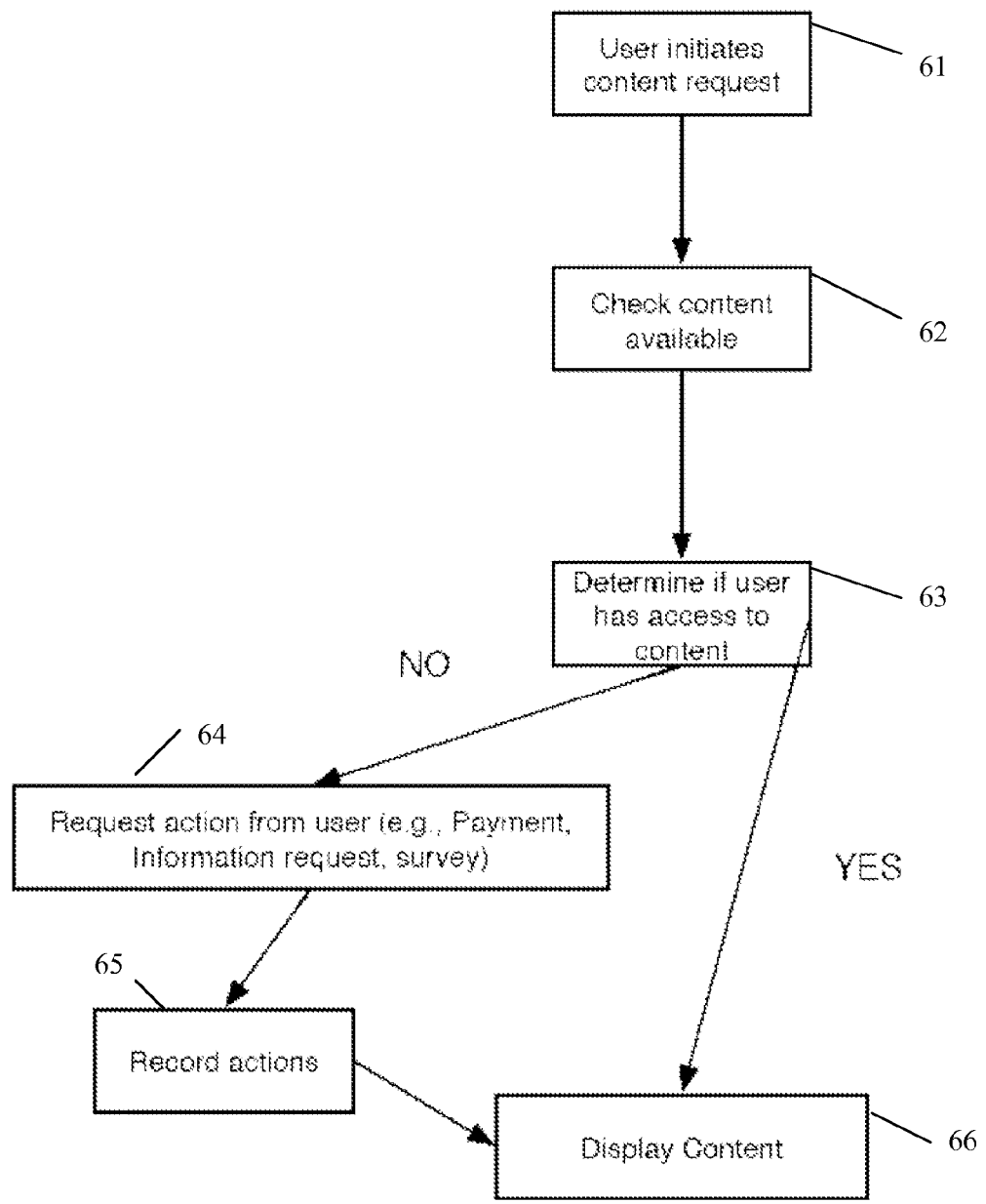
FIG. 6 discloses a reward and payment system for content display.

Similarly, there may need to be a process to reward the content originator for the production of content as shown in FIG. 6. This process may have the ability to motivate the content originator to produce or aggregate content which is appropriate to the end-User.

The User first initiates a content request in step 61. This content request may be implicit or explicit. For example, the User may touch a button requesting content, or the system of the present invention may alert the User that there is new content available. Or, for example, the User may enter a geography, for example, which alerts the system of the present invention to search for content from the content originator.

The system of the present invention checks the database to see if content is available or use another search condition to check the database in step 62. The system of the present invention searches the User history to determine if the User has access to the content in step 63. For example, there may be groups of Users who are in a specific class, for example, who have paid more. Or, for example, the User may have purchased only a limited amount of content. Or, for example, the content originator may have designated a User or set of Users to allow them to have access to content. If the criteria exists in step 63, the system of the present invention will display the content in step 66.

If the User does not have access to the content and if the criteria does not exist in step 63, the system of the present invention may request the User to perform an action as shown in step 64. Such action may be, but not limited to, answering a survey, making a payment, going to a location, etc. The action will then be recorded in step 66 after it is performed and the system of the present invention will display the content in step 66.

For example, a User wants to find out what a rock-star's next big song or solo album release will be. The User may request the information from the system of the present invention. The system of the present invention may check to see if the User has any content requests left. If not, the system of the present invention may alert the User that the User must pay additional money to the system of the present invention to view this content. Or, conversely, the system of the present invention may alert the User that the User needs to visit a specific advertiser's location and make a content request from that location, thereby pushing traffic to that advertiser. 6.4 and 6.41

Figure 7:
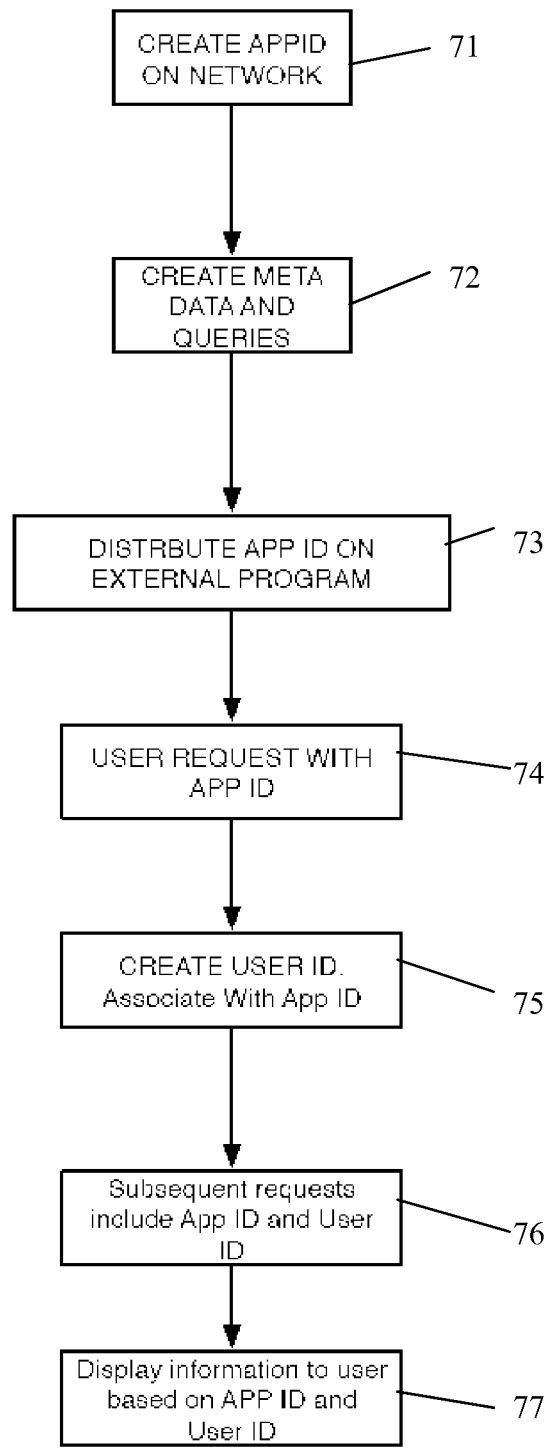
FIG. 7 discloses a flow diagram of Simple ID System.

The system of the present invention may be designed in such a way to allow for quick development of an Application 10 using a simple ID system as shown in FIG. 7. An admin or content originator 12 may add a record on a database on a network that would be related to a new Application 10 in step 71. Meta data would also be entered at this time in step 72, such as the name of the Content Originator 12, name of the Application 10, if the Application 10 is related to any other Apps, etc.

When the Application 10 is distributed to Users in step 73, the Application 10 would contain the ID to associate this ID with the Content Originator 12. When a User accesses the Application 10, a request to the network is initiated with the Application 10 ID as shown in step 74. The system of the present invention generates an identifier that is associated with the Application 10 in step 75. Subsequent requests includes the Application 10 ID and User ID as shown in step 76. In step 77, the system of the present invention uses these two data elements to determine information to display to the User.

As an example of how the above system can be used, someone who is suffering from diabetes would indicate that they are suffering from cancer. The system would display content that is customized to cancer. Additionally, the system would obtain information from them related to what type of cancer and also ask questions related to their current disease state. If the individual indicated they are receiving stem cell treatment, the system would display information related to stem cell treatment. Additionally, the system would continuously request information on how the stem cell treatment is going and display the appropriate information. For example if the User indicated that they have an infection, the system would display the appropriate customized content (related to cancer, infection, and their name, geography, individual). Again, the system would first search for content at the most specific level and broaden its search until the content existed. Additionally, the system would may take geography into account.

Although the present invention has been described in considerable detail with reference to certain preferred versions thereof, other versions are possible. Therefore, the point and scope of the appended claims should not be limited to the description of the preferred versions contained herein.

As to a further discussion of the manner of usage and operation of the present invention, the same should be apparent from the above description. Accordingly, no further discussion relating to the manner of usage and operation will be provided.

The above illustration provides many different embodiments or embodiments for implementing different features of the invention. Specific embodiments of components and processes are described to help clarify the invention. These are, of course, merely embodiments and are not intended to limit the invention from that described in the claims.

Although the invention is illustrated and described herein as embodied in one or more specific examples, it is nevertheless not intended to be limited to the details shown, since various modifications and structural changes may be made therein without departing from the spirit of the invention and within the scope and range of equivalents of the claims. Accordingly, it is appropriate that the appended claims be construed broadly and in a manner consistent with the scope of the invention, as set forth in the following claims.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

The embodiments of the invention in which an exclusive property or privilege is claimed are defined as follows:

1. A computer implemented method for content collection and distribution, the method comprising:
a computer performs the following steps:
choosing a content originator;
creating a content request;
requesting content from the content originator;
providing content items by a content originator;
querying a database of content to display;
providing a request to a content originator
determining which content applies to the requesting user;
determining if other information is needed from the user to display content;
requesting additional information from the user to determine the content to display;
selecting appropriate and available content to display to a user;
collecting user content requests to request content from a content originator;
aggregating user content requests to request content from a content originator;
triaging user content requests to request content from a content originator;
including a keyword in the content by the content originator;
searching the content for keywords or other indicators that are pre-defined;
adding the content for keywords or other indicators that are pre-defined;
executing a pre-defined script after identifying the keyword trigger;
processing the content according to pre-defined processes; and
signaling the occurrence to overtly notify the user that content exists.

2. The method of claim 1, wherein the requested content form the content originator is performed by an explicit action of a user.

3. The method of claim 2, further comprising the step of:
providing a one-touch method for the user to explicitly request content from the content originator.

4. The method of claim 1, wherein the requested content form the content originator is performed by an implicit action of a user.

5. The method of claim 1, further comprising the step of:
requesting additional explicit or implicit information.

6. The method of claim 1, further comprising the step of:
aggregating past and on-going content for later display from the content originator.

7. The method of claim 1, further comprising the step of:
prioritizing the amount of content that exists; and
comparing past behavior of other users to the current user making the request.

8. The method of claim 1, further comprising the step of:
excluding content to a user based on their history, behavior, class or otherwise.

9. The method of claim 1, further comprising the step of:
displaying content to a user based on their history, behavior, class or otherwise.

10. The method of claim 1, further comprising the step of:
providing an ID system for the Content Collection and Distribution System.

11. The method of claim 1, further comprising the step of:
initiating a machine running a program, or
downloading a mobile application to a machine capable of executing the application;
executing the application on a network or via the application which is on a local computer machine running the application, both powered by the system of the present invention.

12. The method of claim 1, further comprising the step of:
creating sub-content items from the content items submitted by a content provider; and
selecting specific sub-content by a user.

13. The method of claim 1, further comprising the step of:
searching past content using a latitude and longitude field; and
querying to determine if there is content related to the content originator related to that geography.

14. The method of claim 1, further comprising the step of:
presenting a general question included with the information request;
answering the question by the user;
storing the answer in a database for later use;
sorting the answer by category or topic;
providing an information request by a user to a content originator;
sorting the information request by a user to a content originator;
using the stored answer; and
determining additional information from the content originator based on the provided and stored answer.

15. The method of claim 14, further comprising the step of:
receiving many requests on a specific topic;
determining the relevant content originator;
sending this request to a content originator;
receiving content in response to the request from a content originator; and
storing the content in a database.

16. The method of claim 15, further comprising the step of:
triaging requests that match a specific criteria;
determining the triage based on a specific keyword, topic, or based on the user; and
sending triaged requests to a content originator.

17. The method of claim 1, further comprising the step of:
supplying a request via audio, visual, or video input from a user;
extracting a list of content items related to a content originator that match exactly or match approximately the information supplied by the user; and
stacking the relevant content items as a query in the database, and list the sub-set of topics and/or questions to which the content relates.

18. The method of claim 1, further comprising the step of:
presenting the content originator with a series of questions,
requesting a topic, more questions, or the display of content by the content originator;
displaying the results;
querying a database of topics from other content originators and display this list to the content originator;
add his or her own questions by the content originator;
answering these questions and topics by the content originator; and
assigning display content to request questions and request topics.

19. The method of claim 1, further comprising the step of:
matching requests to past user history or data;
narrowing down the list of topics using previous logs on topics which the user has requested; and
determining the optimal content to display.

20. The method of claim 1, further comprising the step of:
including a keyword push in the content by the content originator; and
notifying the user that content exists.

21. The method of claim 1, further comprising the step of:
sending an information request to the content originator, where the content originator can respond;
receiving a response from the content originator with new content;
sorting the new content in the database; and
alerting a user that the new content now exists.

22. The method of claim 1, further comprising the step of:
querying the database for content that the user has and hasn't seen;
checking against a user content history for what the user has and hasn't seen;
returning the query results for questions and topics in;
displaying the questions and or topics;
displaying content and content topics and questions that the user has not seen; and
allowing the user to see all content, regardless if he or she has seen the content previously.

23. The method of claim 1, further comprising the step of:
using a criteria to determine if content should be displayed to the user or if additional questions or topics should be displayed to the user before content is displayed;
determining what content is available; and
using the content to create a content sub-set to determine what to display next to the User or what question to ask the User next.

24. The method of claim 23, wherein the criteria includes:
determining the amount of content available; and
determining past user preferences.

25. The method of claim 1, further comprising the step of:
providing a reward to the content originator for the production of content or aggregation of content which is appropriate to the user.

26. The method of claim 1, further comprising the step of:
connecting to a third party acting as a content originator;
obtaining from the third party acting as the content originator as a result of the content request.

27. The method of claim 26, further comprising the step of:
connecting to a third party acting as a content originator which is either: an electronic medical record, medical device, or diagnostic device; and
obtaining medical data from the electronic medical records, medical device, or diagnostic device acting as the content originator as a result of the content request.

* * * * *